United States Patent [19]
De Ponti et al.

[11] Patent Number: 5,804,209
[45] Date of Patent: Sep. 8, 1998

[54] BIOADHESIVE STARCHES AND PROCESS FOR THEIR PREPARATION

[75] Inventors: Roberto De Ponti; Alessandro Martini, both of Milan; Lorena Muggetti, Meda, all of Italy

[73] Assignee: Pharmacia S.p.A., Milan, Italy

[21] Appl. No.: 592,301

[22] PCT Filed: May 30, 1995

[86] PCT No.: PCT/EP95/02044

§ 371 Date: Feb. 9, 1996

§ 102(e) Date: Feb. 9, 1996

[87] PCT Pub. No.: WO95/34582

PCT Pub. Date: Dec. 21, 1995

[30] Foreign Application Priority Data

Jun. 16, 1994 [GB] United Kingdom .................... 9412064
Feb. 1, 1995 [GB] United Kingdom .................... 9501936

[51] Int. Cl.$^6$ ............................. A61F 13/00; A61K 9/14; A61K 9/16; C08B 30/00
[52] U.S. Cl. .................... 424/434; 425/435; 425/489; 425/490; 425/491; 425/492; 425/493; 425/494; 127/65; 127/71
[58] Field of Search ..................................... 424/434, 435, 424/489, 490, 491, 492, 493, 494; 127/65, 71

[56] References Cited

U.S. PATENT DOCUMENTS 3,025,217 3/1962 Bernstein etal. .......................... 167/82
5,204,108 4/1993 Illum ....................................... 424/434

FOREIGN PATENT DOCUMENTS 0 449 782 10/1991 European Pat. Off. .
1148114 7/1986 Japan .
2 237 510 5/1991 United Kingdom .

OTHER PUBLICATIONS

Database WPI, Derwent Publications Ltd., JP A 61 148 114, Jul. 5, 1986.

Junginger et al, Deutsche Apotheker Zeitung, "Bioadhasive Arzneistoffabgabesystem", vol. 130, No. 15, pp. 791–801.

*Primary Examiner*—Marian C. Knode
*Assistant Examiner*—Ali R. Salimi
*Attorney, Agent, or Firm*—Nikaido Marmelstein Murray & Oram LLP

[57] ABSTRACT

The present invention relates to bioadhesive starches, to a process for their preparation and to pharmaceutical compositions containing them. It also relates to the use of such bioadhesive starches as carriers for the administration of a drug.

17 Claims, No Drawings

BIOADHESIVE STARCHES AND PROCESS FOR THEIR PREPARATION

This application is a 371 of PCT/EP95/02044 filed May 30, 1995.

The present invention relates to bioadhesive starches, to a process for their preparation and to pharmaceutical compositions containing them. It also relates to the use of such bioadhesive starches as carriers for the administration of a drug.

In the administration of a drug it may be important to maintain the pharmaceutical dosage form for a sufficiently long time in a suitable place for the absorption. As reported by Duchene D. et al. in "Drug Development and Industrial Pharmacy" 14 (2&3), 283–318 (1988), bioadhesion could lead to the solution of bioavailability problems resulting from a too short stay of the pharmaceutical dosage form at the absorption or activity level of the active ingredient. In the same article bioadhesion is defined "as the ability of a material (synthetic or biological) to adhere to a biological tissue for an extended period of time. This definition includes a large number of adhesion phenomena: the adhesion of various shellfish on rocks, the adhesion of cells on one another, and the adhesion of microorganisms on various mucosa substrates. . . . For bioadhesion to occur, a succession of phenomena is required, whose role depends on the bioadhesive nature. Bioadhesion stages can be summarized as follows. First an intimate contact must exist between the bioadhesive and the receptor tissue. This contact results either from a good wetting of the bioadhesion surface, or from the swelling of the bioadhesive. When contact is established, the penetration of the bioadhesive into the crevice of the tissue surface then takes place, or interpenetration of bioadhesive chains with those of the mucus. Low chemical bonds can then settle."

J. R. Robinson in U.S. Pat. Nos. 4,615,697 and 4,795,436, both named "Bioadhesive Compositions and Methods of Treatment Therewith" describes the use of "water-swellable but water-insoluble, fibrous, cross-linked carboxy-functional polymer, said polymer containing (a) a plurality of repeating units of which at least about 80 percent contain at least one carboxyl functionality, and (b) about 0.05 to about 1.5 percent cross-linking agent substantially free from polyalkenyl polyether, said percentages being based upon the weights of unpolymerized repeating unit and cross-linking agent, respectively."

In these Robinson's patents the use of synthetic, cross-linked polymers is done to obtain good bioadhesive properties. In the present invention the materials used are only derived from natural products by very simple physical modifications. Considering the safety, the use of a natural product like starch vs. a synthetic polymer has to be considered an improvement. The carboxyl functionality present in the Robinson's bioadhesives may also give stability problems due to the marked chemical reactivity of carboxyl functionality. This functionality is also very sensible to the pH of the environment, producing different bioadhesive patterns depending on pH. Modified starches have been described in the scientific and patent literature for their bioadhesive properties in particular to give buccal; controlled-release, bioadhesive dosage forms.

Bioadhesive starches obtained by spray-drying or drum-drying are reported by Bottenberg P., et al., "Development and Testing of Bioadhesive, Fluoride-containing Slow-release Tablets for Oral Use", J. Pharm. Pharmacol., 1991, 43: 457–464. In this article formulations were prepared starting from, among other polymers, "drum-dried waxy maize (DDWM, mol. wt 4.000.000) and spray-dried waxy maize (SDWM, mol. wt 4.000.000) (Cerestar, Vilvoorde, Belgium)". The article concludes "that bioadhesive polymers such as thermally modified corn starch with 5% polyacrylic acid or polyethylene glycol (mol. wt 300.000) can be used as a slow-release device for fluoride. The system we describe is a positive step in the development of dose-efficient fluoride administration in the oral cavity."

The same first author had previously filed a patent application: Bottenberg P., Remon J. P., De Muynck C., "Composition of a bioadhesive sustained delivery carrier for drug administration", European Patent Application No. 90870055.2. In this application it is disclosed a "Composition of a bioadhesive carrier for administration of a drug ensuring a prolonged, sustained and controlled delivery of said drug, characterized in that it contains pregelatinized or thermally modified starches, preferably precooked and dried starches" (lines 56 through 58 page 5) as well as the "Use of pregelatinized, or thermally modified, preferably precooked and dried starches to formulate a gel or a drug releasing platform with good bioadhesive properties" (claim 9, lines 20–21, page 6). In the cited EPA 90870055.2, one can read, in lines 28 through 41, page 2: "Pregelatinization is easily obtained by:

spray-drying: these products consist of distorted hollow spheres, usually with an air cell enclosed at the center. They are made by first cooking the starch in water and then by spraying the hot paste in a hot chamber or tower;

roll dried: particles appear as transparent, flat irregular platelets. In general these products are simultaneously cooked and dried on heated rolls, using either a closely set pair of squeeze rolls or a single roll with a closely set doctor blade. In either case, a paperthin flake, which is then ground to the desired mesh size, is obtained;

extruded or drum-dried: individual particles from either process are much thicker and more irregular in dimensions than roll-dried products. Drum-drying is similar to roll-drying except that a thicker coating of starch paste is applied to heated rolls, and the dried product is then ground to the desired particle size. In the extruded process, moistened starch is forced through a super heated chamber under very high shear, then "exploded" and simultaneously dried by venting at atmospheric pressure". Pregelatinized starches are commercially available (e.g. Cerestar supply), obviously at higher prices compared to waxy starches or native starches.

We have surprisingly found that bioadhesive starches can be obtained from non bioadhesive starches by grinding or milling.

Grinding or milling is a very simple and cheap process which does not require an expensive equipment and a complicated procedure compared to drum-drying, spray-drying and extrusion.

The present invention provides a process for obtaining bioadhesive starches, the process comprising high energy grinding or high energy milling of non bioadhesive starches.

Non bioadhesive starches may be, for example, native starches.

Native starches are starches extracted from vegetables such as graminaceous or leguminosal, for example, maize starch, wheat starch, rice starch or such as tuberous, for example, potatoes starch or manioc starch. Native starches have different amylose/amylopectine ratio. When the amylopectine content is about 100%, the starches are defined as "waxy".

We have found that the grinding process induces bioadhesive properties in a non bioadhesive starch only if it is performed in high-energy mills such as, for example a high-energy ball mill, a high-energy vibrating mill or a high-energy rod mill.

A hammer mill or a pin mill which aren't high energy mill are unable to induce bioadhesive properties in non bioadhesive starches: see table III below.

The high energy grinding or high energy milling may be performed on dry materials at a thermostated temperature ranging from about −20° C. to about room temperature for a time varying from about 1 hour to about 12 hours.

In order to evaluate the modifications induced by our technologies on native starches or waxy starches, molecular weight determinations by intrinsic viscosity measurements have been carried out.

What was surprisingly found is that the bioadhesive starches we have obtained are structurally quite different from the ones on the market that possess this property (e.g. Cerestar SF12410, pregelatinized starch).

In fact the intrinsic viscosity value and, as a consequence, the molecular weight of these new materials are quite lower than that of the known commercial products.

The molecular weight of the new bioadhesive starches can be modulated, such as their bioadhesive properties, by a careful control of the grinding procedure.

We have also compared the bioadhesive starches obtained by the process of the invention to the bioadhesive starches obtained by a spray-drying technique which is one of the traditional pregelatinization processes as described, e.g., in the cited European Patent Application No. 90870055.2.

We have found that the starches obtained by the process of the invention have better bioadhesive properties compared to the bioadhesive starches obtained by a spray-drying technique.

A further object of the invention are pharmaceutical compositions comprising a bioadhesive starch of the invention and a biologically active substance and, optionally, one or more inert excipients.

The active drug may be added to the biohadesive starch obtained by the process of the invention or grinded or milled together with the starch.

The bioadhesive starches of the invention are able to maintain an active substance, for a sufficiently long time, in a place suitable for the absorption.

Therefore a further object of the invention is a drug delivery system comprising a bioadhesive starch of the invention as a carrier. In particular, the bioadhesive starches of the invention are useful as carriers for administration of a drug ensuring a prolonged, sustained and controlled delivery of said drug.

The invention also provides the use of the bioadhesive starches of the invention to formulate a gel or a drug delivery platform with bioadhesive properties.

Any active drug substance may be used in the composition of the present invention.

Examples of drugs are:

proteins and peptides such as, e.g., insulin (hexameric/dimeric/monomeric forms), glucagon, growth hormone (somatotropin), calcitonins and synthetic modification thereof, enkephalins, interferons (especially alpha-2 interferon for treatment of common colds), luteinising hormone-releasing hormone (LHRH) and analogues (Nafarelin, Buserelin, Leuprorelin, Goserelin), GHRH (growth hormone releasing hormone), secretin, bradykinin antagonists, GRF (growth releasing factor), THF (thymic humoral factor), TRH (thyrotropin releasing hormone), ACTH analogues, IGF (insulin-like growth factors), CGRP (calcitonin gene related peptide), atrial natriuretic peptide, vasopressin and analogues (DDAVP, lypressin), nasal vaccines (particularly AIDS vaccines), FACTOR VIII;

antibiotics and antimicrobial agents such as, e.g., tetracycline hydrochloride, leucomycin, penicillin, penicillin derivatives and erythromycin, chemotherapeutic agents such as, e.g., sulphathiazole and nitrofurazone; local anaesthetics such as, e.g., benzocaine; vasocontrictors such as, e.g., phenylephrinehydrochloride, tetrahydrozoline hydrochloride, naphazoline nitrate, oxymetazoline hydrochloride and tramazoline hydrochloride; cardiotonics such as, e.g., digitalis and digoxin; vasodilators such as, e.g., nitroglycerin and papaverine hydrochloride; antiseptics such as, e.g., chlorhexidine hydrochloride, hexylresorcinol, dequalinium chloride; bone metabolism controlling agents such as, e.g., vitamin $D_3$ and active vitamin $D_3$; sex hormones; hypotensives; sedatives; anxiolytics and anti-tumor agents; antidiabetics such as, e.g., glipizide and other sulphonilureas; calcium-antagonist such as, e.g., nifedipine; CNS agents such as, e.g., reboxetine, ondansetron and the like, nicergoline, metoclopramide, fentanyl, migraine treatment drugs like, e.g., dihydroergotamine, ergometrine, ergotamine;

steroidal anti-inflammatory agents such as, e.g., hydrocortisone, prednisone, fluticasone, prednisolone, triamcinolone, triamcinolone acetonide, dexamethasone, betamethasone, beclomethasone, and beclomethasone diproprionate; non-steroidal anti-inflammatory agents such as acetaminophen, aspirin, aminopyrine, phenylbutazone, mefenamic acid, ibuprofen, ibufenac, alclofenac, diclofenac sodium, indomethacin, colchicine, probenecid, phenactin, sulpyrine, sulfenamic acid; enzymatic anti-inflammatory agents such as chymotrypsin and bromelain seratiopeptidase; anti-histaminic agents such as diphenhydramine hydrochloride, chloropheniramine maleate and clemastine; anti-allergic agents; antitussive-expectorant; antiasthmatic agents such as, e.g., sodium cromoglycate, codeine phosphate, and isoproterenol hydrochloride.

Other examples of active substances may be steroids, for instance medroxyprogesterone acetate (MPA), progesterone, testosterone, 6-methyleneandrosta-1, 4-diene-3,17-dione and the like; antibiotics such as, e.g., gentamicin, griseofulvin, cefalosporins, penems and the like; antidepressant drugs such as, e.g., benzodiazepins, e.g., temazepam, oxazepam, diazepam, nitrazepam and the like; immunomodulators such as, e.g., 2-cyano-3-(1,4-dihydro-1-phenyl-(1)-benzothiopyran) (4,3-C)-pyrazol-3yl-3-oxo-N-phenylpropanamide and the like; antiinflammatory agents such as, e.g., indoprofen, ketoprofen, flufenamic acid and the like; antineoplastic agents such as, e.g., anthracycline glycosides, e.g., doxorubicin, epirubicin, idarubicin (i.e. 4-dimethoxy daunorubicin) and 3'-desamine-3'-(3-cyano-4-morpholinyl)-doxorubicin and the like, etoposide, teniposide and other podophyllotoxins, and also nicotine.

The compositions are particularly suitable for the administration of physiologically active polypeptides. All possible isomers, stereoisomers and optical isomers of drugs and their mixtures may be used in the compositions of the present invention. Metabolites and metabolic precursors of bioprecursors of drugs may also be used. The relative proportions and dosages of the components in the compositions will vary with the nature of the components, the route of administration, the frequency of administration and the age, weight and condition of the patient.

The compositions may be suitable for administration by nasal, oral, rectal, buccal, transdermal, intestinal, tracheal, broncheal, pulmonary, or vaginal routes. Particularly interesting is the use of the biohadesive starches of the invention for the administration of a drug by nasal route.

In the nasal administration of a drug, the ciliary movement in the nasal mucosa tends to remove the drug from the absorption site. This problem is overcome by using a bioadhesive material as carrier. The bioadhesive material increases the permanence time in the nasal cavity and a better absorption of a drug is obtained. For example, the bioadhesive starches of the invention can be used as carriers in the nasal administration of temazepan, glipizide or THF.

The compositions of the invention may further comprise additional ingredients which are conventionally found in such compositions, for instance suitable excipients, as well as lubricants, binders, dyes, odor improvers, preservatives and surface-active agents. They may be used, especially, when bioadhesive properties are indicated to improve the residence time of the formulation, or to localize and target the administration, and generally to modify the bioavailability profile of the active drug substance.

The term bioadhesion describes a phenomenon in which synthetic or biological macromolecules and hydrocolloids are able to adhere to a biological tissue.

The force of bioadhesion is the interfacial force which holds together the adhesive material and the biological tissue.

Numerous techniques for the determination of bioadhesion could be used. The bioadhesive properties of our materials have been examined with a simple and predictive rheological test recently described by Caramella et al. (Proceed. Intern. Symp. Control. Rel. Bioact. Mater. 20, 1993 pp. 240–41). According to this experimental protocol, the rheological interaction between bioadhesive polymers and mucin has been proposed as a means for evaluating the mucoadhesive properties of different polymers, taking into consideration the viscosity parameters of mucin and of its mixtures with polymers. The data have been confirmed by means of a tensile stress method, as described by Ferrari et al. (Proceed. $14^{th}$ Pharmaceutical Technology Conference, 1995 (2) pp.99–110).

Grinding Procedures

Grinding processes have been carried out with different milling apparatus from laboratory to pilot-plant scale. Lab scale experiments have been carried out with a Giuliani IGW2 high energy ball mill equipped with porcelain balls in a 300 mL jar. The jar was carefully thermostated during the process.

The Sweco Vibro-Energy® mill Model DM-3 has been used as an high energy vibrating pilot-plant scale mill.

The Bantham CF with horizontal shaft has been utilized as an hammer mill.

The Alpine 100 UPZ has been used as a pin mill.

Spray-Drying Procedures

For spray-drying processes, a Lab-Plant SD-04 has been used.

A 5% suspension in water of the starch was spray-dried at two different inlet temperatures maintaining constant the other variables such as the outlet temperature (between 80°–90° C.) the diameter of the nozzle (0.5 mm) and the blower pressure (1.25 Kg/cm$^2$). After the process the powder obtained was sieved.

Bioadhesion Evaluation

In order to appreciate the extent of the rheological interaction with mucin, isoviscous solutions (having similar apparent viscosities in a given shear rate range) of the different polymers were examined as mentioned previously (Caramella et al., Proceed. Intern. Symp. Control. Rel. Bioact. Mater. 20, 1993 pp. 240–41.).

Viscosimetric tests (according to Hassan et al., Pharm. Res. 7, 1990 pp. 491–495) were performed on polymer solutions and on their mixtures with mucin.

Rheological tests have been performed using a Bohlin CS Rheometer Apparatus equipped with coaxial cylinder and cone plate measuring systems.

As standards two commercial polymers have been used, one with already known bioadhesive properties (Pregelatinized Starch), the other with no detectable bioadhesive characteristics (Waxy Starch).

The tests performed have surprisingly shown that the grinding process induces bioadhesive properties in a non-bioadhesive starch as a waxy Starch polymer is.

In the following Tables (I to IV), rheological synergism between polymer batches and mucin (expressed in Pascal*second) is shown versus different applied shear rates.

As rheological synergism we mean the difference between the observed viscosity of the mixture of the polymer batch with the mucin and a theoretical value, calculated as the sum of the viscosity of the mucin and the viscosity of the polymer solution alone.

The comparisons are made on isoviscous samples.

The following batches are used in the experiments:

| A | Pregelatinized Starch | (supplied by Cerestar) |
|---|---|---|
| B | Waxy Starch | (supplied by Cerestar) |

Tensile Stress Test

The bioadhesion potential of the different samples was determined by means of a tensile stress tester, previously described in Ferrari et al., Proceed. $14^{th}$ Pharmaceutical Technology Conference, 1995 (2) pp. 99–110. The apparatus is assembled in a horizontal supporting base. It basically consists of a load cell (mod. 524, DS Europe, Milan, I), which is solidal with a movable carriage and is connected to a personal computer via an amplifier (mod. DS 467 EA, DS Europe, MIlan, I). The carriage can be moved on two rods, which are fixed on the supporting plane. A motor, equipped with a speed transformer, moves a screw, which in turn pushes on the load cell: the movement is thus transmitted to the carriage. A LVDT transducer (RS n. 649- 599, RS Supplies, Corby, U.K.) is also linked to the movable carriage and is connected via an amplifier (RS Transducer Conditioner Type OD3, Corby, U.K.) to the same personal computer. The LVDT transducer is calibrated by means of a micrometric device to assess the relationship between the electric output (V) and the displacement (mm). At the beginning of the experiment, 50 mg of the polymer solution, previously hydrated in distilled water to reach a 25% weight/weight concentration, were applied on a filter paper disc, which was attached using double-sided adhesive tape to the sample holder. Another filter paper disc was fixed, faced to the polymer sample, on the movable carriage, and was hydrated with 40 µL of a 4% weight/weight mucin dispersion. The carriage was then moved until contact between the paper discs were established. Afterwards, a preload of 800 mN was applied on the sample by threading a special device (consisting of a piston surrounded by a calibrated spring) against the moveable carriage. The preload value was chosen as the minimum force value capable to ensure an even contact between the two surfaces (mucin dispersion and polymer sample). After a three minut rest, the preload was removed and the movable carriage was moved forward at a constant speed up to complete separation of the two surfaces.

Both displacement (measured with the LVDT transducer), and force of detachment (with the load cell) were simultaneously collected and recorded by the computer. Force versus displacement curves were subsequently analyzed in order to obtain maximum force of detachment and to calculate the work of adhesion (in accordance with the trapezoidal rule). Tensile measurements were also performed using 40 µL of distilled water instead of the mucin dispersion (blank test).

The data were expressed as the work of adhesion ratio between the polymer/mucin mixtures and the polymer/water mixtures. Values higher than 1.00 were obtained when bioadhesion occured.

Intrinsic Viscosity Measurements

The intrinsic viscosity measurements on the samples were carried out in NaOH 0.5M at 20° C. as described by Burchard in Makromolecular Chemie, 1963, pp. 110–125.

As clearly depicted in table I, the pregelatinized Starch, is has for its own bioadhesive interaction with mucin whereas the waxy Starch is absolutely a non bioadhesive polymer (negative rheological interaction with mucin).

In table II the bioadhesive performances of various batches of grinded waxy Starch are analyzed and compared. It is evident that high energy ball milling is effective in transforming starch inducing bioadhesive properties. The bioadhesive properties of the materials increases with the time of milling. The possibility to carefully control the grinding temperature is an additional advantage for the reproducibility of the process.

When the waxy Starch is spray dried, no changes in bioadhesive properties are evident remaining the interaction with mucin negative (table II).

The results after an hammer milling indicate that the shear forces are ineffective in inducing bioadhesive properties in starch polymers (table III).

When a bigger high-energy mill, like Sweco Vibro-Energy® mill, is used bioadhesive properties in waxy Starch are induced (table IV). The following examples illustrate but do not limit the invention.

Example 1

A 12 gram amount of waxy starch (B) was put in the Giuliani IGW2 high energy ball mill with 83.4 grams of spherical shaped grinding media (diameter 7 mm) made of porcelain. The powder was ground for 6 hours. During the process the grinding camera was thermostated at +18° C. A sample obtained from the above mentioned process was analyzed for its bioadhesive properties as previously described (Paragraphs "Bioadhesion Evaluation" and "Tensile Stress Test").

The results (Table II) show that the grinded product has higher positive interaction compared to the initial properties of the starch used.

Example 2

A 12 gram amount of waxy starch (B) was put in the Giuliani IGW2 high energy ball mill with 83.4 grams of spherical shaped grinding media (diameter 7 mm) made of porcelain. The powder was ground for 3 hours. During the process the grinding camera was thermostated at +18° C. A sample obtained from the above mentioned process was analyzed for its bioadhesive properties as previously described (Paragraphs "Bioadhesion Evaluation" and "Tensile Stress Test").

The results (Table II) show that the grinded product has higher positive interaction compared to the initial properties of the starch used.

Example 3

A 2 kilogram amount of waxy starch (B) was put in the Sweco Vibro-Energy® mill with 60 kilos of cylindrical shaped grinding media (height 12.7 mm, base radius 6.3 mm) made of high density alumina. The powder was ground for 3 hours.

A sample obtained from the abovementioned process was analyzed for its bioadhesive properties as previously described (Paragraphs "Bioadhesion Evaluation" and "Tensile Stress Test").

The results (Table IV) show that the grinded product has higher positive interaction compared to the initial properties of the starch used.

Example 4

A 2 kilogram amount of waxy starch (B) was put in the Sweco Vibro-Energy® mill with 60 kilos of cylindrical shaped grinding media (height 12.7 mm, base radius 6.3 mm) made of high density alumina. The powder was ground for 6 hours.

A sample obtained from the abovementioned process was analyzed for its bioadhesive properties as previously described (Paragraphs "Bioadhesion Evaluation" and "Tensile Stress Test").

The results (table IV) show that the grinded product has higher positive interaction compared to the initial properties of the starch used.

Example 5

A 180 gram amount of waxy starch (B) was ground using the Bantham CF hammer mill with horizontal shaft equipped with a screen with a nominal aperture size of 1.539 $mm^2$.

A sample obtained from the abovementioned process was analyzed for its bioadhesive properties as previously described (Paragraphs "Bioadhesion Evaluation" and "Tensile Stress Test").

The results (Table III) show that the grinded product has no higher interaction compared to the initial properties of the starch used. The results showed that shear stress milling did not lead to a bioadhesive starch.

Example 6

A 270 gram amount of waxy starch (B) was ground using the Bantham CF hammer mill with horizontal shaft equipped with a screen with a nominal aperture size of 3.125 $mm^2$.

The sample was not analyzed for the bioadhesive properties because it was qualitative determined that also at more stressed process conditions the starch obtained was not bioadhesive.

Example 7

A 230 gram amount of waxy starch (B) was ground using the Alpine 100 UPZ pin mill. The loading was 60 gram/minute the grinding camera speed 15750 raws per minute.

A qualitative evaluation of the powder gave indication that the starch obtained was not bioadhesive, showing again that shear stress milling is not suitable to obtain bioadhesive starch.

Example 8

A 230 gram amount of waxy starch (B) was ground using the Alpine 100 UPZ pin mill. The loading was 60 gram/minute the grinding camera speed 8750 raws per minute.

A qualitative evaluation of the powder gave indication that the starch obtained was not bioadhesive, showing again that shear stress milling is not suitable to obtain bioadhesive starch.

Example 9

A suspension in water containing 5% of waxy starch (B) was spray-dried using a Lab-Plant SD-04 equipment. The process parameters were set as follows: inlet temperature 170° C.; outlet temperature 85° C.; blower pressure 1.25 $Kg/cm^2$; nozzle diameter 0.5 mm.

A sample was analyzed for its bioadhesive properties as previously described (Paragraph "Bioadhesion Evaluation"). The results (Table II) show that the spray-dried product has a the same interaction with mucin when compared to the initial properties of the starch used. In this case the spray drying process did not lead to any change in the bioadhesive properties of starch.

Example 10

A 1 kilogram amount of waxy starch (B) ground as described in Example 4 was mixed with 0.7 kilogram of Temazepam (Carlo Erba Reagenti, Milan, I). The mixture was put in the Sweco Vibro-Energy® mill with 60 kilos of cylindrical shaped grinding media (height 12.7 mm, base radius 6.3 mm) made of high density alumina. The powder was ground for 1 hour.

A sample obtained from the abovementioned process was analyzed for its bioadhesive properties as previously described (Paragraph "Bioadhesion Evaluation").

The results (table V) show that there is a positive interaction with mucin.

Example 11

A 1 kilogram amount of waxy starch (B) was mixed with 0.7 kilogram of Temazepam (Carlo Erba Reagenti, Milan, I). The mixture was put in the Sweco Vibro-Energy® mill with 60 kilos of cylindrical shaped grinding media (height 12.7 mm, base radius 6.3 mm) made of high density alumina. The powder was ground for 6 hours.

A sample obtained from the abovementioned process was analyzed for its bioadhesive properties as previously described (Paragraph "Bioadhesion Evaluation").

The results (table V) show that there is a positive interaction with mucin.

Example 12

A 180 gram amount of waxy starch (B) ground as described in Example 4 was mixed with 120 grams of Temazepam (Carlo Erba Reagenti, Milan, I). The mixture was compressed and granulated in dry conditions according to well known pharmaceutical procedures.

Example 13

A 11.94 gram amount of waxy starch (B) ground as described in Example 1 or 4 was mixed with 0.06 grams of THF (Farmitalia Carlo Erba, Milan, I). The mixture was put in the Giuliani IGW2 high energy ball mill with 83.4 grams of spherical shaped grinding media (diameter 7 mm) made of porcelain. The powder was ground for 1 hour. During the process the grinding camera was thermostated at +18° C.

Example 14

A 11.94 gram amount of waxy starch (B) ground as described in Example 1 or 4 was mixed with 0.06 grams of THF (Farmitalia Carlo Erba, Milan, I) using a suitable mixer till homogeneity has been reached.

Example 15

A 9 gram amount of waxy starch (B) was mixed with 3 grams of glipizide (Antibioticos, Rodano (Milan), I). The mixture was put in the Giuliani IGW2 high energy ball mill with 83.4 grams of spherical shaped grinding media (diameter 7 mm) made of porcelain. The powder was ground for 6 hours.

Example 16

A 9 gram amount of waxy starch (B) as described in Example 1 or 4 was mixed with 3 grams of glipizide (Antibioticos, Rodano (Milan), I) using a suitable mixer till homogeneity has been reached.

TABLE I

| Shear rate (1/sec) | A | B |
|---|---|---|
| | Rheological Synergism (Pa * sec) | |
| 50 | 0.47 | −0.34 |
| 100 | 0.40 | −0.26 |
| 150 | 0.36 | −0.21 |
| 200 | 0.34 | −0.17 |
| 250 | 0.33 | −0.14 |
| Tensile Stress Test | 1.77 | 0.86 |
| Intrinsic viscosity (g/dL) | 1.28 | 2.08 |

A  Pregelatinized Starch  (supplied by Cerestar)
B  Waxy Starch     (supplied by Cerestar)

TABLE II

| Shear rate (1/sec) | Ex. 2 | Ex. 1 | Ex. 9 | B |
|---|---|---|---|---|
| | Rheological Synergism (Pa * sec) | | | |
| 50 | 0.18 | 0.62 | −0.36 | −0.34 |
| 100 | 0.14 | 0.57 | −0.20 | −0.26 |
| 150 | 0.12 | 0.52 | −0.14 | −0.21 |
| 200 | 0.12 | 0.50 | −0.10 | −0.17 |
| 250 | 0.12 | 0.48 | −0.08 | −0.14 |
| Tensile Stress Test | 1.46 | 1.71 | not done | 0.86 |
| Intrinsic viscosity (g/dL) | 1.52 | 0.61 | 1.97 | 2.08 |

Ex. 2 Waxy Starch - grinding in a Giuliani IGW2 high energy ball mill for 3 hours at 18° C.
Ex. 1 Waxy Starch - grinding in a Giuliani IGW2 high energy ball mill for 6 hours at 18° C.
Ex. 9 Waxy Starch - Spray dried - inlet 170° C.
B    Waxy Starch (supplied by Cerestar)

TABLE III

| Shear rate (1/sec) | Example 5 | B |
|---|---|---|
| | Rheological Synergism (Pa * sec) | |
| 50 | −0.35 | −0.34 |
| 100 | −0.16 | −0.26 |
| 150 | −0.10 | −0.21 |
| 200 | −0.07 | −0.17 |
| 250 | −0.04 | −0.14 |
| Tensile Stress Test | 0.88 | 0.86 |
| Intrinsic viscosity (g/dL) | 1.80 | 2.08 |

Ex. 5  Waxy Starch - grinding in a Bantham CF hammer mill
B     Waxy Starch (supplied by Cerestar)

TABLE IV

| Shear rate (1/sec) | Example 3 | Example 4 | B |
|---|---|---|---|
| | Rheological Synergism (Pa * sec) | | |
| 50 | 0.65 | 1.21 | −0.34 |
| 100 | 0.49 | 1.03 | −0.26 |
| 150 | 0.42 | 0.90 | −0.21 |
| 200 | 0.38 | 0.86 | −0.17 |
| 250 | 0.35 | 0.82 | −0.14 |
| Tensile Stress Test | 1.50 | 1.55 | 1.86 |
| Intrinsic viscosity (g/dL) | 1.28 | 0.88 | 2.08 |

Ex. 3 Waxy Starch - grinding in a Sweco Vibro-Energy ® mill for 3 hours
Ex. 4 Waxy Starch - grinding in a Sweco Vibro-Energy ® mill for 6 hours
B    Waxy Starch (supplied by Cerestar)

TABLE V

| Shear rate (1/sec) | Example 10 | Example 11 | B |
|---|---|---|---|
| | Rheological Synergism (Pa * sec) | | |
| 50 | 1.13 | 0.30 | −0.34 |
| 100 | 0.86 | 0.21 | −0.26 |

TABLE V-continued

| Shear rate (1/sec) | Example 10 | Example 11 | B |
|---|---|---|---|
| | Rheological Synergism (Pa * sec) | | |
| 150 | 0.69 | 0.18 | −0.21 |
| 200 | 0.60 | 0.17 | −0.17 |
| 250 | 0.56 | 0.15 | −0.14 |

Ex. 10 Waxy Starch ground an Temazepam - cogrinding in a Sweco Vibro-Energy ® mill for 1 hour
Ex. 11 Waxy Starch and Temazepam - cogrinding in a Sweco Vibro-Energy ® mill for 6 hours
B Waxy Starch (supplied by Cerestar)

What is claimed is:

1. A process for preparing a bioadhesive starch, which comprises grinding or milling a non bioadhesive starch in a high energy ball mill, a high energy rod mill, or a high energy vibrating mill.

2. The process according to claim 1 wherein the non bioadhesive starch is a native starch.

3. The process according to claim 1 wherein the non bioadhesive starch is a waxy starch.

4. The process according to claim 1 wherein the high energy grinding or high energy milling is performed at a thermostated temperature from about −20° C. to about room temperature.

5. The process according to claim 1 wherein the high energy grinding or high energy milling is performed for a time ranging from about 1 hour to about 12 hours.

6. The bioadhesive starch produced by the process of claim 1.

7. A pharmaceutical composition comprising a biologically active substance and the bioadhesive starch according to claim 6.

8. The pharmaceutical composition according to claim 7 further comprising one or more pharmaceutically acceptable excipients.

9. A pharmaceutical composition according to claim 7, wherein the biologically active substance is temazepam, glipizide or thymic humoral factor (THF).

10. A method of delivering a drug to a person in need of such drug comprising administering to the person the drug with a carrier, wherein the carrier is the bioadhesive starch according to claim 6.

11. A gel or a drug releasing platform with bioadhesive properties comprising the bioadhesive starch according to claim 6.

12. A method of delivering a drug to a tissue surface comprising
applying a medicament to the tissue surface, wherein said medicament comprises the drug and the bioadhesive starch according to claim 6.

13. A medicament for delivering a drug to a tissue surface, wherein the medicament comprises the drug and the bioadhesive starch according to claim 6.

14. A process for preparing a bioadhesive pharmaceutical composition of a biologically active substance which comprises grinding or milling a non bioadhesive starch with the said biological substance, optionally in admixture with one or more pharmaceutical acceptable excipients, in a high energy ball mill, a high energy rod mill, or a high energy vibrating mill.

15. A method for controlling the degree of bioadhesiveness of a starch which was originally non-bioadhesive, comprising grinding or milling the non-bioadhesive starch in a high energy ball mill, a high energy rod mill, or a high energy vibrating mill for a sufficient length of time to impart the degree of bioadhesiveness to the starch.

16. A method for controlling the degree of bioadhesiveness of a pharmaceutical composition comprising a biologically active substance and a starch which was originally non-bioadhesive, the method comprising grinding or milling the non-bioadhesive starch with the biological substance, optionally in admixture with one or more pharmaceutical acceptable excipients, in a high energy ball mill, a high energy rod mill, or a high energy vibrating mill for a sufficient length of time to impart the degree of bioadhesiveness to the pharmaceutical composition.

17. The method according to claim 10 wherein the drug is administred nasally.

* * * * *